(12) United States Patent
Liukkonen et al.

(10) Patent No.: US 11,453,961 B2
(45) Date of Patent: Sep. 27, 2022

(54) METHOD AND APPARATUS FOR MANUFACTURING NATURAL FIBER BASED STAPLE FIBERS ON A COMMON SURFACE

(71) Applicant: Spinnova Oy, Jyväskylä (FI)

(72) Inventors: Johanna Liukkonen, Jyväskylä (FI);
Sanna Haavisto, Jyväskylä (FI); Pasi Selenius, Lievestuore (FI); Juha Salmela, Laukaa (FI); Janne Poranen, Muurame (FI); Arto Salminen, Jyskä (FI); Marko Myllys, Jyväskylä (FI); Pia Vento, Vaajakoski (FI); Karri Björklund, Jyväskylä (FI)

(73) Assignee: SPINNOVA OY, Jyväskylä (FI)

( * ) Notice: Subject to any disclaimer, the term of this patent is extended or adjusted under 35 U.S.C. 154(b) by 333 days.

(21) Appl. No.: 16/481,168

(22) PCT Filed: Feb. 15, 2018

(86) PCT No.: PCT/FI2018/050115
§ 371 (c)(1),
(2) Date: Jul. 26, 2019

(87) PCT Pub. No.: WO2018/150099
PCT Pub. Date: Aug. 23, 2018

(65) Prior Publication Data
US 2019/0390375 A1    Dec. 26, 2019

(30) Foreign Application Priority Data
Feb. 15, 2017 (FI) .................................. 20175134

(51) Int. Cl.
*B23K 26/00* (2014.01)
*B26D 3/16* (2006.01)
(Continued)

(52) U.S. Cl.
CPC ............ *D01G 1/04* (2013.01); *B23K 26/083* (2013.01); *B23K 26/0823* (2013.01);
(Continued)

(58) Field of Classification Search
CPC .. B23K 26/00; B23K 26/0823; B23K 26/083; B23K 26/0838; B23K 26/0846;
(Continued)

(56) References Cited

U.S. PATENT DOCUMENTS

| 3,556,969 A | 1/1971 | Mizuguchi et al. |
| 3,740,940 A | 6/1973 | Berkowitch |

(Continued)

FOREIGN PATENT DOCUMENTS

| AU | 2008344471 B2 | 12/2012 |
| CN | 101215725 A | 7/2008 |

(Continued)

OTHER PUBLICATIONS

Finnish Patent and Registration Office, search report of Finnish Application No. 20175134, dated Apr. 28, 2017, 2 pages.

*Primary Examiner* — Leo B Tentoni
(74) *Attorney, Agent, or Firm* — ArentFox Schiff LLP

(57) ABSTRACT

The application relates to a method and apparatus for manufacturing a natural fiber based staple fibers. The application further relates to the staple fibers, staple fiber based raw wool and products comprising such. A method comprises providing a cellulose suspension (101, 310, 510) including water, refined cellulose fibrils and at least one rheology modifier, directing the cellulose suspension through a nozzle (102, 320, 520) onto a surface (300, 400, 500), drying the cellulose suspension onto the surface (103, 300, 400, 500) for forming a fiber (350, 550), and cutting the cellulose suspension on the surface for forming staple fibers (105).

16 Claims, 6 Drawing Sheets

(51) Int. Cl.

| | |
|---|---|
| *B26F 3/08* | (2006.01) |
| *B26F 3/16* | (2006.01) |
| *B28B 1/26* | (2006.01) |
| *D01D 5/253* | (2006.01) |
| *D01G 15/00* | (2006.01) |
| *D01G 15/02* | (2006.01) |
| *F26B 3/04* | (2006.01) |
| *F26B 3/06* | (2006.01) |
| *F26B 3/08* | (2006.01) |
| *F26B 3/22* | (2006.01) |
| *F26B 3/24* | (2006.01) |
| *F26B 13/14* | (2006.01) |
| *F26B 13/16* | (2006.01) |
| *F26B 13/18* | (2006.01) |
| *D01G 1/04* | (2006.01) |
| *D01F 2/00* | (2006.01) |
| *D01D 5/04* | (2006.01) |
| *D01F 4/02* | (2006.01) |
| *D01D 5/26* | (2006.01) |
| *D01D 10/02* | (2006.01) |
| *D01F 1/10* | (2006.01) |
| *D01F 4/00* | (2006.01) |
| *D01D 7/00* | (2006.01) |
| *D01H 1/00* | (2006.01) |
| *B23K 26/08* | (2014.01) |
| *B26D 7/08* | (2006.01) |
| *B29C 69/00* | (2006.01) |
| *A61L 24/10* | (2006.01) |
| *D02G 3/02* | (2006.01) |
| *D21H 17/25* | (2006.01) |
| *D21H 21/28* | (2006.01) |
| *A61L 15/32* | (2006.01) |
| *B26D 7/01* | (2006.01) |

(52) U.S. Cl.
CPC ...... *B23K 26/0838* (2013.01); *B23K 26/0846* (2013.01); *B26D 7/086* (2013.01); *B29C 69/001* (2013.01); *D01D 5/04* (2013.01); *D01D 5/26* (2013.01); *D01D 7/00* (2013.01); *D01D 10/02* (2013.01); *D01F 1/10* (2013.01); *D01F 2/00* (2013.01); *D01F 4/00* (2013.01); *D01F 4/02* (2013.01); *D01H 1/00* (2013.01); *F26B 13/145* (2013.01); *F26B 13/183* (2013.01); *A61L 15/325* (2013.01); *A61L 24/102* (2013.01); *B26D 2007/013* (2013.01); *B29C 2793/00* (2013.01); *B29C 2793/009* (2013.01); *B65H 2701/31* (2013.01); *D02G 3/02* (2013.01); *D21H 17/25* (2013.01); *D21H 21/28* (2013.01); *Y10T 442/633* (2015.04)

(58) Field of Classification Search
CPC .... B26D 3/16; B26D 2007/013; B26D 7/086; B26F 3/08; B26F 3/16; B28B 1/26; B29C 69/001; B29C 2793/00; B29C 2793/009; B65H 2701/31; D01D 5/253; D01D 5/26; D01D 7/00; D01D 10/02; D01F 2/00; D01G 1/04; D01G 15/00; D01G 15/02; F26B 3/04; F26B 3/06; F26B 3/08; F26B 3/22; F26B 3/24; F26B 13/14; F26B 13/145; F26B 13/16; F26B 13/18; F26B 13/183
USPC ........ 264/86, 141, 143, 163, 177.13, 211.12, 264/234; 425/84, 174, 174.2, 174.4, 310, 425/315, 376.1, 382.2, 461; 19/0.46, 19/0.56, 98; 34/108, 110, 385, 623; 83/913
See application file for complete search history.

(56) References Cited

U.S. PATENT DOCUMENTS

| | | | | |
|---|---|---|---|---|
| 3,744,361 | A | * | 7/1973 | Van Doorn ............... D01G 1/04 83/913 X |
| 3,831,473 | A | * | 8/1974 | Fleissner .................. D01G 1/04 83/913 X |
| 5,591,388 | A | | 1/1997 | Sellars et al. |
| 6,075,177 | A | * | 6/2000 | Bahia ................ A61F 13/00008 602/43 |
| 9,322,117 | B2 | | 4/2016 | Salmela et al. |
| 2006/0124261 | A1 | * | 6/2006 | Lindsay ................. D21H 21/18 162/117 |
| 2007/0225631 | A1 | | 9/2007 | Bowlin et al. |
| 2011/0200776 | A1 | | 8/2011 | Zikeli et al. |
| 2014/0121622 | A1 | | 5/2014 | Jackson et al. |
| 2014/0331893 | A1 | | 11/2014 | Salmela et al. |
| 2017/0233536 | A1 | | 8/2017 | Purcell et al. |

FOREIGN PATENT DOCUMENTS

| | | |
|---|---|---|
| CN | 101220571 A | 7/2008 |
| CN | 101654813 A | 2/2010 |
| CN | 102560735 A | 7/2012 |
| CN | 105392929 A | 3/2016 |
| FI | 955630 A | 11/1995 |
| GB | 489272 A | 7/1938 |
| GB | 1025273 A | 4/1966 |
| JP | 09501471 A | 2/1997 |
| JP | 2006-110393 A | 4/2006 |
| JP | 2009221615 A | 10/2009 |
| JP | 2014-510845 A | 5/2014 |
| RU | 2139962 C1 | 1/1995 |
| RU | 2139962 C1 | 10/1999 |
| WO | 95/194465 A1 | 7/1995 |
| WO | 9519465 A1 | 7/1995 |
| WO | 2009084566 A1 | 7/2009 |
| WO | 2011128322 A2 | 10/2011 |
| WO | 2012107643 A2 | 8/2012 |
| WO | 2013034814 A1 | 3/2013 |
| WO | 2013150258 A1 | 10/2013 |
| WO | 2015158955 A1 | 10/2015 |
| WO | 2016102782 A1 | 6/2016 |

* cited by examiner

METHOD AND APPARATUS FOR MANUFACTURING NATURAL FIBER BASED STAPLE FIBERS ON A COMMON SURFACE

PRIORITY

This application is a U.S national application of the international application number PCT/FI2018/050115 filed on Feb. 15, 2018 and claiming priority of Finnish application 20175134 filed on Feb. 15, 2017 the contents of all of which are incorporated herein by reference.

TECHNICAL FIELD

The present application relates to staple fibers and staple fiber based raw wool, a method for manufacturing such and an apparatus for manufacturing such. Further, the application relates to a surface for forming staple fibers for fiber based raw wool. Further, the application relates to yarn and non-woven manufactured of staple fibers or fiber based raw wool.

BACKGROUND

Products, like yarn and fabric, may be made of natural or synthetic starting material. Synthetic starting material may pose negative effects on recyclability or disposing phases of products. Natural starting material may pose negative environmental effects during its growth or processing. Example of such natural starting material is cotton.

SUMMARY

It is an object of the application to provide natural fiber based raw wool. Aim is to provide ecological natural fiber based raw wool, which is processable as raw wool in order to make yarn or non-woven. Another object is to provide natural fiber based staple fibers. The staple fibers may be for raw wool.

According to an aspect of the invention natural fiber based raw wool comprises staple fibers, which have been shortened twice.

A cellulose suspension comprises an aqueous suspension of water and cellulose. Additionally the cellulose suspension may comprise at least one rheology modifier. Cellulose comprises natural fibers. The cellulose suspension is directed through a nozzle onto a surface for drying. The cellulose suspension is dried by removing water from the cellulose suspension. Thereby a natural fiber is formed on the surface, for example on a belt or a wire or a cylinder surface.

The natural fiber is extracted from the surface. The natural fiber may be shortened into staple fibers of a certain length in order to make raw wool. This may be implemented on the surface or after extracted from the surface. The natural fiber based raw wool comprises staple fibers of certain length. Staple fibers are arranged in random order in order to form a raw wool network comprising staple fibers of certain length. The natural fiber based raw wool comprises staple fibers in fluffy, airy, loose arrangement such that order and density of the staple fibers among the natural fiber based raw wool is uneven. The natural fiber based raw wool comprises unhomogenous structure. A staple fiber based raw wool may be processed in order to provide yarn or non-woven material.

According to an aspect of the invention a method for manufacturing natural fiber based staple fibers comprises providing a cellulose suspension including water and refined cellulose fibrils. The method further comprises directing the cellulose suspension through a nozzle onto a surface, drying the cellulose suspension onto the surface, cutting the cellulose suspension on the surface for forming staple fibers.

An apparatus for manufacturing natural fiber based staple fibers according to an aspect of an invention comprises a nozzle arranged to direct a cellulose suspension including aqueous refined cellulose fibrils onto a surface. The apparatus further comprises a dryer arranged to dry the cellulose suspension on the surface for forming a fiber. The cellulose suspension is arranged to be cut on the surface in order to form staple fibers.

According to an aspect of the invention a method for manufacturing a natural fiber based raw wool comprises providing a cellulose suspension including water and refined cellulose fibrils. The method further comprises directing the cellulose suspension through a nozzle onto a surface, drying the cellulose suspension onto the surface for forming a fiber, and extracting the fiber form the surface in order to form a natural fiber based raw wool comprising staple fibers.

An apparatus for manufacturing a natural fiber based raw wool according to an aspect of an invention comprises a nozzle arranged to direct a cellulose suspension including aqueous refined cellulose fibrils onto a surface. The apparatus further comprises a dryer arranged to dry the cellulose suspension on the surface for forming a fiber, and extractor arranged to extract the fiber form the surface in order to form a fiber based raw wool comprising staple fibers.

An aspect of the invention relates to a surface for forming staple fibers from a cellulose suspension comprising aqueous suspension of refined cellulose fibrils. The surface comprises a radius of curvature of 0.25-4 m; and grooves aligned on the surface perpendicular to the direction of movement of the surface. Grooves may be placed at predetermined constant intervals.

The grooves on the surface may be replaced by other kind of discontinuation places. Discontinuation places may comprise ridges or grooves. Discontinuation places may comprise cut-outs, inlays, slots, channels, crests, indentations, grooves, ridges, protrusions, projections or other kind of discontinuation places. Alternatively the cellulose suspension may be arranged to be cut or shortened into staple fibers on the surface by means for cutting. Means for cutting may comprise exposing the cellulose suspension to a radiation, to a substance, or other means for cutting.

An aspect of an invention relates to a fiber based raw wool manufactured according to previous manufacturing method and/or apparatus. A fiber based raw wool comprising staple fibers, wherein the staple fibers are comprised of refined cellulose fibrils interlocked by hydrogen bonds and the fiber based raw wool comprises unoriented, entangled, fluffy network of staple fibers.

An aspect of the invention relates to a yarn made of staple fiber based raw wool. Another aspect of the invention relates to a non-woven material made of staple fiber based raw wool.

DESCRIPTION OF DRAWINGS

In the following embodiments of the invention are described with the accompanying figures of which

DESCRIPTION OF EMBODIMENTS

Figure 1:
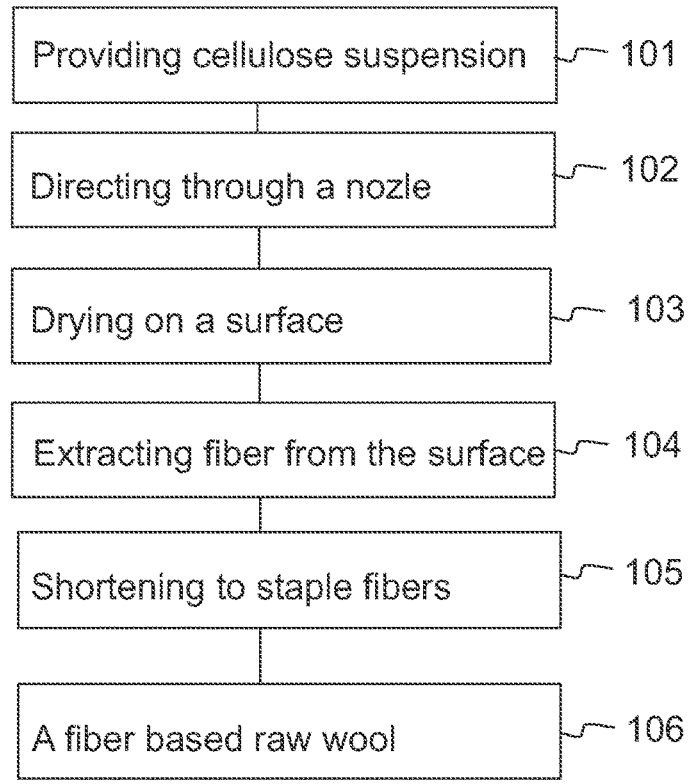
FIG. 1 illustrates a method for manufacturing a fiber based raw wool according to an embodiment.

FIG. 1 illustrates a method for manufacturing a natural fiber based raw wool according to an embodiment. A cellulose suspension is provided 101. The cellulose suspension comprises aqueous suspension of refined cellulose fibrils. The cellulose suspension may comprise water, refined cellulose fibrils and at least one rheology modifier. Fibrils of the cellulose suspension originate from shortened or refined pulp or plant based material. The cellulose suspension is directed through a nozzle 102. The nozzle feeds the cellulose suspension to a surface. The surface may be a surface of a belt, of a wire or of a cylinder. The cellulose suspension is dried on the surface 103. Drying removes water from the cellulose suspension. The dried cellulose suspension is arranged to form a fiber onto the surface. The fiber may be arranged in a form of a continuous fiber. The continuous fiber is extracted from the surface 104. The fiber extracted from the surface is cut or shortened in order to form staple fibers 105. The stable fibers are arranged to form an unhomogenous network comprising fiber concentrations of varying density and orientation. The unhomogenous fluffy material of staple fibers is called a natural fiber based raw wool 106.

Figure 2:
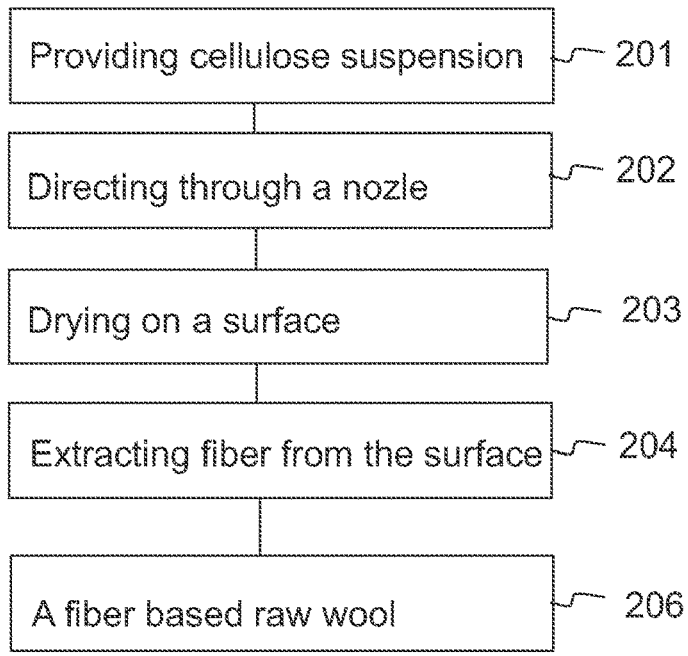
FIG. 2 illustrates a method for manufacturing a fiber based raw wool according to an embodiment.

FIG. 2 illustrates a method for manufacturing a natural fiber based raw wool according to an embodiment. A cellulose suspension is provided 201. The cellulose suspension comprises aqueous suspension of refined cellulose fibrils. The cellulose suspension may comprise water, at least one rheology modifier and refined cellulose fibrils. Refined cellulose fibrils may originate from plant based pulp. The cellulose suspension is directed through a nozzle 202. The nozzle feeds the cellulose suspension to a surface, for example on a surface of a belt, or of a wire or of a cylinder. The cellulose is arranged to be shortened and dried on the surface 203. The dried and shortened cellulose suspension is arranged to form staple fibers. This is enabled by grooves arranged on a curved surface. The shortened fibers are extracted from the surface 204. The stable fibers are arranged to form an unhomogenous network comprising fiber concentrations of varying density and orientation. The unhomogenous fluffy material of staple fibers is called a natural fiber based raw wool 206.

The grooves on the surface may be replaced by cut-outs, inlays, slots, channels, crests, indentations, grooves, ridges, protrusions, projections or other kind of discontinuation places. In an alternative implementation cellulose suspension is arranged to be shortened on the surface by cutting means. The cutting means may comprise laser, heat, chemicals, ultrasound, for example.

A cellulose suspension comprises cellulosic fibrils. Cellulosic fibrils are natural fibrils originating from plant based material source. Plant based fibrils may comprise virgin or recycled plant material or combinations of such. Plant based fibrils may originate from wood or non-wood material. Plant may comprise wood, for example hardwood, like birch, aspen, poplar, alder, eucalyptus, acacia, or softwood, like spruce, pine, fir larch, doular-fir, hemlock. Alternatively or in addition cellulose fibrils may originate from other non-wood plants, for example cotton, hemp, flax, sisal, jute, kenaf, bamboo, peat, coconut. Non-wood cellulosic fibril or fiber may originate from agricultural residues, grasses, straw, leaves, bark, seeds, hulls, flowers, vegetables or fruits.

Additionally suspension may comprise virgin or recycled fibers originating from synthetic materials, such as glass fibers, polymeric fibers, metal fibers or from natural materials, such as wool fibers, or silk fibers.

Cellulose is an organic compound comprising linear chains of D-glucose units linked through β-(1,4)glucosidic bonds. Cellulosic fibrils comprise organic fibrils. Cellulose fibrils may comprise plant based fibrils. Cellulose fibrils may comprise wood based fibers. Cellulose fibrils in native form refer to natural cellulose fibrils. Natural cellulose fibrils have not undergone chemical modification of the cellulose polymer structure. A paper pulp is an example of a mix of natural cellulose fibrils. Cellulose is a linear polysaccharide polymer with several glucose monosaccharide units. Natural cellulose fibrils may be separated from a plant- or wood based raw material in chemical or mechanical pulping process. The pulp comprises cellulosic fibrous material. Natural wood based fibers are composed of fibrils of cellulose in a matrix of hemicellulose and lignin.

Cellulosic fibrils may originate from nanocellulose comprising nano-structured cellulose i.e. nanosized cellulose fibrils. There are several widely used synonyms for nano-structured cellulose. For example: nanocellulose, nanofibrillated cellulose (NFC), cellulose nanofibrils (CNF), microfibrillar cellulose, nanofibrillar cellulose, cellulose nanofiber, nano-scale fibrillated cellulose, microfibrillated cellulose (MFC), or cellulose microfibrils (CMF). Nanocellulose fibrils comprise a high aspect ratio, being the length to width ratio. Nanocellulose fibrils may comprise width or lateral dimensions of less than 200 nanometers, preferably between 2-20 nanometers, more preferably between 5-12 nanometers. Nanocellulose fibrils may comprise length or longitudinal dimension from one to several micrometers, for example.

Nanocellulose fibrils may be isolated from any cellulose-containing material, for example wood pulp. The dimensions of fibrils or fibril bundles are dependent on raw material and isolation method. The nanocellulose fibrils may be isolated from wood based fibers through high pressure, high temperature and high velocity impact homogenization. The homogenization process is used to delaminate or disintegrate the cell walls of the fibers and to liberate their sub-structural fibrils and micro fibrils. Enzymatic and/or mechanical pre-treatments of wood fibers may also be used. Nanocellulose fibrils may be chemically pre-modified, for example N-oxyl mediated oxidation.

Cellulose fibrils may be in native form, which have not undergone any chemical modification. Natural cellulose fibers and natural cellulosic fibrils may be non-regenerated. Thus, natural cellulose fibers/fibrils have not undergone chemical regeneration or physical modification of the cellulose polymer structure. Natural cellulose fibers/fibrils are non-regenerated and consists mainly of crystalline structure of cellulose I. Cellulose I may have structures $I_\alpha$ and $I_\beta$. Man-made cellulosic fibers are regenerated and crystalline structure is mainly other than cellulose I. Conversion of cellulose I to cellulose II (or other forms, like cellulose III or cellulose IV) is irreversible. Thus, these forms are stable and cannot be converted back to cellulose I.

The nanofibrillated cellulose may also contain some hemicelluloses; the amount is dependent on the plant source. Mechanical disintegration of microfibrillar cellulose from cellulose raw material, cellulose pulp, or refined pulp is carried out with suitable equipment such as a refiner, grinder, homogenizer, colloider, friction grinder, ultrasound sonicator, fluidizer such as microfluidizer, macrofluidizer or fluidizer-type homogenizer.

Cellulosic fibers may be isolated from any cellulose containing raw material using chemical-, mechanical-, bio-, thermo-mechanical-, or chemi-thermo-mechanical pulping process. Mechanically shortened, refined or cut fibers may comprise chemically or physically modified derivative of cellulose micro fibrils or fibril bundles.

Nanocellulose fibrils may be isolated from any cellulose-containing material. The cellulose-producing microorganism may be of the genus *Acetobacter, Agrobacterium, Rhizobium, Pseudomonas* or *Alcaligenes,* preferably of the genus *Acetobacter* and more preferably of the species *Acetobacter xylinum* or *Acetobacter pasteurianus*.

Nanofibrillar cellulose may be any chemically or physically modified derivate of cellulose nanofibrils or nanofibril bundles. The chemical modification may be based for example on carboxymethylation, oxidation, esterification, or etherification reaction of cellulose molecules. Modification may be realized by physical adsorption of anionic, cationic, or non-ionic substances or any combination of these on cellulose surface. Any modification may be carried out before, after, or during the production of microfibrillar cellulose.

The nanofibrillated cellulose may be made of cellulose which is chemically premodified to make it more labile. The starting material of this kind of nanofibrillated cellulose is labile cellulose pulp or cellulose raw material, which results from certain modifications of cellulose raw material or cellulose pulp. For example N-oxyl mediated oxidation (e.g. 2,2,6,6-tetramethyl-l-piperidine N-oxide) leads to very labile cellulose material, which is easy to disintegrate to microfibrillar cellulose. For example patent application WO2009/084566 discloses such modifications. The nanofibrillated cellulose manufactures through this kind of premodification or labilization is called NFC-L for short, in contrast to nanofibrillated cellulose which is made of not labilized or normal cellulose, NFC-N.

The nanofibrillated cellulose may be made of plant material where the nanofibrils may be obtained from secondary cell walls. One example source is wood fibers. The nanofibrillated cellulose is manufactured by homogenizing wood-derived fibrous raw material, which may be chemical pulp. When NFC-L is manufactured from wood fibers, the cellulose is labilized by oxidation before the disintegration to nanofibrils. The disintegration in some of the above-mentioned equipment produces nanofibrils which have the diameter of only some nanometers, which is 50 nm at the most and gives a clear dispersion in water. The nanofibrils may be reduced to size where the diameter of most of the fibrils is in the range of only 2-20 nm only. The fibrils originating in secondary cell walls are essentially crystalline with degree of crystallinity of at least 55%. Microfibrillated cellulose (MFC) is produced in a similar manner than nanofibrillated cellulose (NFC). Dimensions of MFC are between natural pulp fibrils and NFC fibrils.

Cellulose suspension may comprise 80-98 wt-% of water and 2-20 wt-% of cellulose. The cellulose suspension may comprise 85-98 wt-% of water and 2-15 wt % of cellulose. In addition the cellulose suspension may comprise 0-5 wt-% of rheology modifier. The cellulose may be pure cellulose, or comprise hemicellulose and/or lignin, for example. The cellulose suspension comprises microfibrillated cellulose (MFC) or nanofibrillated cellulose (NFC). Cellulose suspension comprises mechanically refined or shortened fibers. At least most of the fibrils are refined in order to have certain length. MFC fibril diameter may be about or less than 100 µm. MFC length weighed average fibril length may be 10-200 µm.

Rheology modifier comprises a compound or agent arranged to modify the viscosity, yield stress and/or thixotropy of the suspension. Rheology modifier may comprise high molecular weight polymers. Rheology modifier is arranged to modify cellulose suspension rheology by adjusting gel strength and yield point of the cellulose suspension. The cellulose suspension comprises strength or storage modulus of 1 000-20 000 Pa. The cellulose suspension comprises yield point of 0.5-5%. Strength and yield point of the cellulose suspension effect on the cellulose suspension achieving high shear thinning. The cellulose suspension comprises viscosity at 1000 1/s of 1-1000 mPas.

A rheology modifier may be at least one of alginic acid, alginate, sodium alginate, pectin, carrageenan, nanofibrillar cellulose, polyethylene oxide (PEO), carboxymethyl cellulose (CMC), starch, polycarboxylic acid, sodium hypophosphite, cationic polyacrylamide (CPAM), anionic polyacrylamide (APAM), polyamide-epichlorohydrin resin (PAE) or combination of such.

Figure 3:
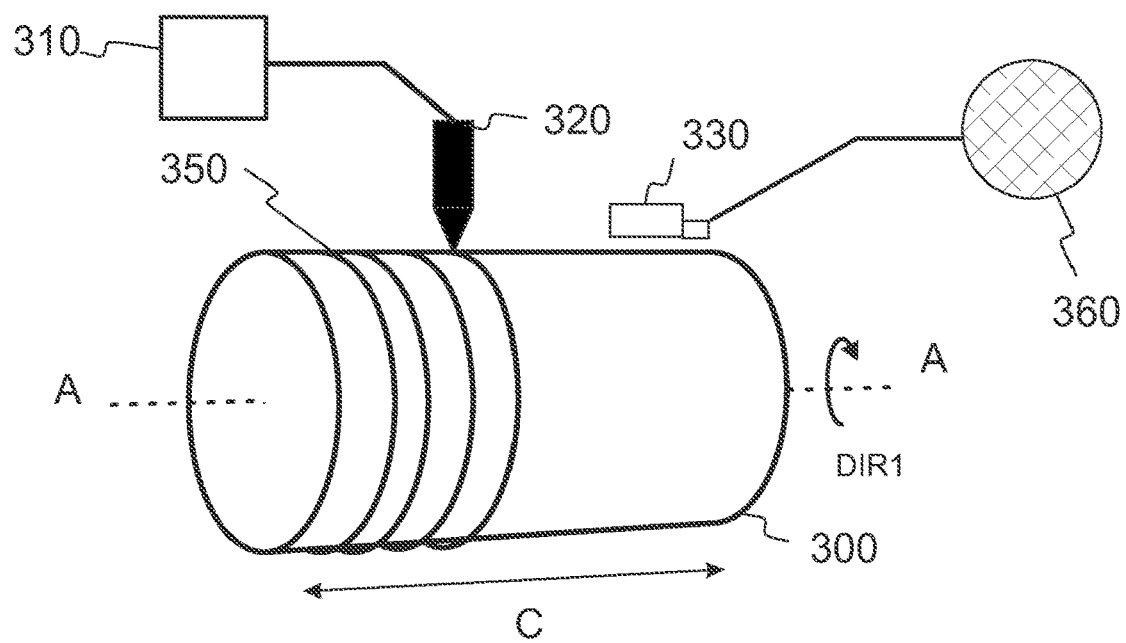
FIG. 3 illustrates an apparatus for manufacturing a fiber based raw wool according to an embodiment.

FIG. 3 illustrates an apparatus for manufacturing natural fiber based raw wool according to an embodiment. A cellulose suspension 310 is fed to a nozzle 320. The refined fibrils of the cellulose suspension align in a nozzle. The aqueous suspension of water and fibrils of the cellulose suspension form an oriented fibril network in a nozzle 320.

The cellulose suspension 310 is directed onto a cylinder 300 via the nozzle 320. The cellulose suspension exiting the nozzle 320 is shaped according to the nozzle outlet opening. The nozzle outlet opening may be shaped as a round or as elliptic, for example. The cellulose suspension exits the nozzle 320 in a form of a continuous strand having a cross-sectional shape corresponding to that of the nozzle outlet opening. The cellulose suspension exiting the nozzle 320 may have round or elliptic cross-sectional shape.

The nozzle 320 may be arranged to move back and forth along the longitudinal direction C, i.e. direction of the rotational axis A, of the cylinder 300, along horizontal plane. The cellulose suspension 310 is directed to a certain horizontal level along the longitudinal cylinder surface. Due to rotation of the cylinder 300 and movement of the nozzle 320, the fed cellulose suspension 310 circles around the cylinder surface forming a round next to a round, or partly overlapping with adjacent rounds. The continuously injected cellulose suspension 310 moves on the surface of the cylinder 300 with the rotating cylinder 300. While the cylinder 300 rotates around its rotational axis A, the nozzle 320 is arranged to move to an adjacent place along longitudinal cylinder surface C.

Alternatively two or more nozzles may be arranged adjacent, parallel along longitudinal cylinder surface C. The two or more nozzles are united, forming an integrated unit, and arranged to move concurrent along longitudinal cylinder surface C. The distance between two adjacent nozzles may be in order of centimeters, for example 1 cm. The nozzle(s) are oscillating along the longitudinal dimension of the cylinder. In case of two or more nozzles arranged at 1 cm distance from each other, the time that the nozzles take to move 1 cm corresponds to drying time of the cellulose suspension injected on the cylinder surface. Moving speed of nozzles is arranged such that time for a length of the dimension between the two adjacent nozzles is arranged to correspond to drying time of the cellulose suspension.

During drying water is removed and fibrils star forming hydrogen bonds. Thereby fiber is formed. Hydrogen bonds are formed as dry content increases from 70 wt-% towards 100 wt-%. Dried cellulose suspension or fiber forming or fiber refer to dry content of at least 70 wt-%. Fiber yarn count comprises 1-20 dtex. Fiber diameter may be 15-70 μm. Fiber tensile strength may be 15-25 cN/tex, preferably 15-20 cN/tex, and comprise stretch or elongation break of 5-15%, preferably 5-10%.

In case of multiple nozzles along the longitudinal dimension of the cylinder, the multiple nozzles may be placed next to each other along the whole longitudinal dimension of the cylinder. Thus, there is no need for movement of nozzles, but those may be fixed in their places. In this case the drying time of the cellulose suspension corresponds to time of rotation of the cylinder.

With two or more nozzles, the cylinder is covered with cellulose suspension and fiber is formed faster than in case of one nozzle. Accordingly extracting fibers, providing oil and other relating functions shall be accomplished at corresponding pace.

The cellulose suspension exit from a nozzle and/or injection onto a surface may be controlled hydraulically or pneumatically. Velocity of the cellulose suspension exiting the nozzle may be controlled by pressure applied on the cellulose suspension at the nozzle.

An oil supply 330 may be placed on a surface of the cylinder 300. The oil supply 330 is arranged to move, in an oscillating manner, as the nozzle 320, along longitudinal dimension of the cylinder 300, parallel with the axis of rotation A of the cylinder 300, at certain vertical level. In case of oscillating nozzle(s) 320 the oil supply 330 is arranged to oscillate simultaneously with the nozzle(s) 320.

Rotation of a cylinder may be controlled externally, for example by an electric motor, whose rotational speed is adjustable. A cylinder or a curved belt may generate a centripetal acceleration of 1-1000 g, preferably 100-500 g. Diameter of a cylinder may be 1-6 m. Rotational speed of the surface of the cylinder may be 5-25 m/s. The centripetal force ($F_{cp}$) acting on suspension (m) is dependent on radius (r) of the cylinder and its rotational surface speed (v). The centripetal force ($F_{cp}$) acting on suspension (m) is dependent on radius (r) of curvature of a belt and its rotational surface speed (v). Mathematically: $F_{cp}=ma=mv^2/r$; wherein $a=v^2/r$.

The cellulose suspension is dried on the surface of the cylinder 300. This may be effected internally and/or externally. Heating internally may be effected via electric heating resistor, heating steam or air. Heating externally may be effected via irradiation, heating and/or air blow. The dried cellulose suspension forms a fiber 350 onto surface of the cylinder 300. The fiber 350 is extracted from the surface of the cylinder 300. Extracting may be based on blowing, suction, vacumization, scraping or dropping fibers from the surface based on gravitation. The fiber 350 may be extracted mechanically or using vacuum or pressurized air. The extraction may be implemented manually or automatically.

An extractor may be placed on a side of the cylinder 300 opposite to the nozzle 320. The extractor may have a fixed place, or the extractor may be arranged to move, in an oscillating manner, as the nozzle 320, along longitudinal dimension of the cylinder 300, parallel with the axis of rotation A of the cylinder 300, at certain vertical level. The extractor is arranged to oscillate simultaneously with the nozzle. The extractor may be integrated with the oil supply 330 and move with it. Oil is supplied on a cylinder surface after the fiber has been extracted from the cylinder surface. Oil may be replaced by other suitable substance, like wax.

The extracted fiber 360 is in form of unoriented and entangled fiber based raw wool, which may comprise uneven clumps among fluffy fiber based raw wool. When the fiber based raw wool comprises continuous fiber, the length of fiber is arranged to be cut or shortened to form staple fibers. After shortening fiber based raw wool comprising staple fibers is formed.

The fiber comprises linear mass density of 1-20 dtex, which relates to an amount of mass per unit length (1 tex=1 g/1000 m; and 1 decitex=1 dtex=1 g/10000 m). Tenacity of the fiber comprises 10-30 cN/tex, preferably 15-25 cN/tex. Tenacity of the fiber comprises 15-25 cN/tex, preferably 15-20 cN/tex.

Stretch to break the fiber is 5-15%, preferably 5-10%. Some of the oil from the drying surface is present in the fiber surface. The oil on the fiber surface has effect on further processing of the fiber based raw wool, for example to the friction and adhesion between fibers of the raw based wool. Oil may be replaced by a suitable substance, for example wax.

Figure 4:
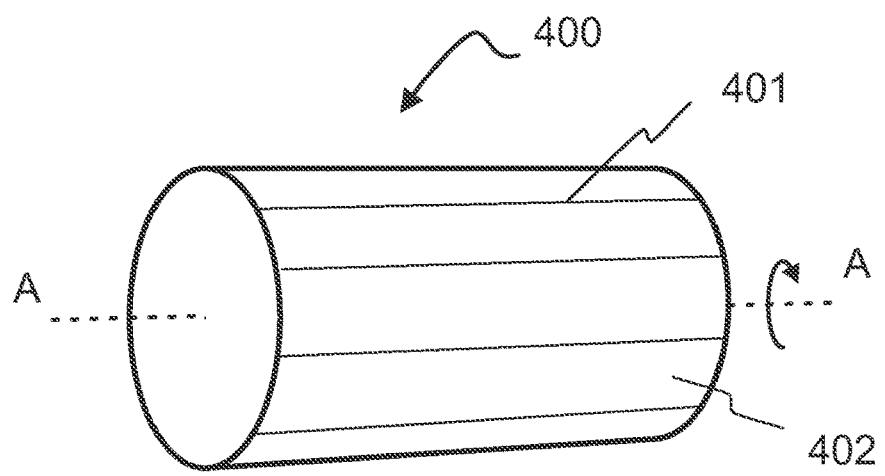
FIG. 4 illustrates a cylinder according to an embodiment.

FIG. 4 illustrates a cylinder according to an embodiment of the invention. FIG. 4 shows axis of rotation A of the cylinder 400. Cylinder may comprise an even, flat external surface or a grooved surface, as illustrated in the FIG. 4. Grooves 401 are arranged onto external surface of the cylinder 400 parallel with the axis of rotation A of the cylinder 400. The injected cellulose suspension is in contact with ridges 402 between the grooves 401 of the cylinder surface. Grooves 401 form a weak point for the cellulose suspension and have effect of forming a discontinuity for the continuously injected cellulose suspension. The continuouosly injected cellulose suspension has a break at each groove. Thereby the cellulose suspension forms separate parts of length of ridges 402 between the grooves 401. After extensive water is dried, staple fiber is formed onto the cylinder, on the ridges 402 between the grooves 401. Length of formed staple fibers is determined by the length between grooves 401 on the cylinder surface.

In case of grooved cylinder, the fiber based raw wool extracted from the cylinder comprises staple fibers. No additional refining, shorting or cutting means or phases are needed. The staple fiber based raw wool is processable. The fiber based raw wool comprises staple fibers, which have been shortened to a predefined length with the aid of grooves. The spacing between the grooves on the cylinder surface determine length of the staple fibers.

The grooves 401 on the surface may be replaced by cut-outs, inlays, slots, channels, crests, indentations, ridges, protrusions, projections or other kind of discontinuation places. The discontinuation places comprise irregular surface shape. The regular, even or steady surface comprises irregularities at certain intervals. The discontinuation places or irregularities of the surface are aligned on the surface perpendicular to the direction of movement of the surface.

The injected cellulose suspension is in contact with regular surface between the discontinuation places, which form a weak point for the cellulose suspension and have effect of forming a discontinuity for the continuously injected cellulose suspension. This causes the continuouosly injected cellulose suspension to cut at each discontinuation place. Thereby the cellulose suspension forms separate parts of length of regular surfaces between the discontinuation places. After extensive water is dried, staple fiber is formed onto the surface, on the regular surface between the discontinuation places. Length of formed staple fibers is determined by the length between the discontinuation places on the surface. Alternatively or in addition, the continuously injected cellulose suspension, when/after dried, may be cut into staple fibers by exposing it to cutting means or an external matter. The external matter or cutting means may relate to radiation, substance or other matter capable of cutting the fiber on the surface. The external matter may comprise laser, infrared, heat, ultrasound, electron beam, water, or chemicals, for example. Cutting into staple fibers may be done during or after the suspension is dried on the surface.

Figure 5:
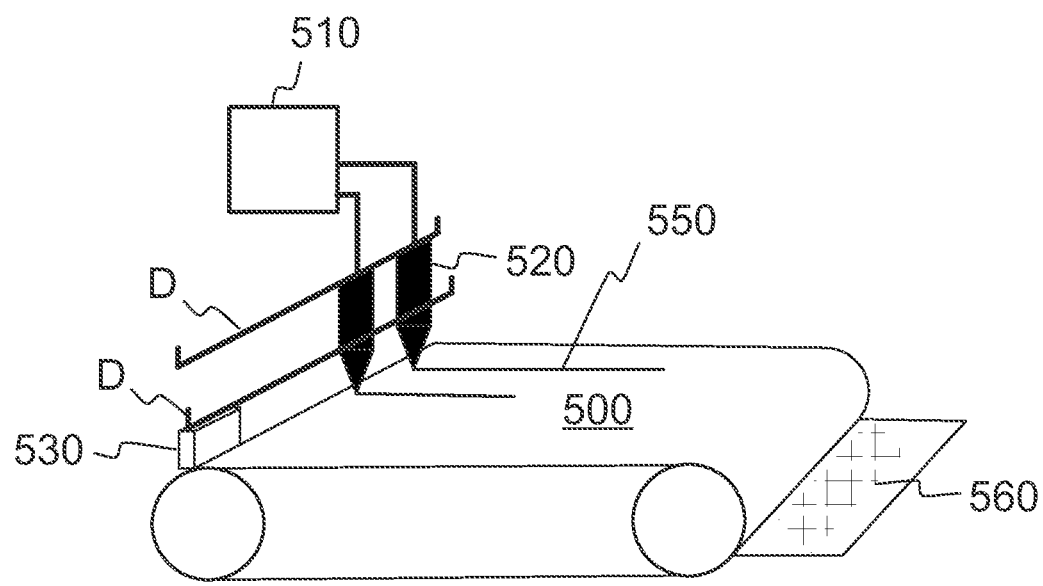
FIG. 5 illustrates an apparatus for manufacturing a fiber based raw wool according to an embodiment.

FIG. 5 illustrates an apparatus for manufacturing natural fiber based raw wool according to an embodiment. A cellulose suspension 510 is fed to a one or more nozzle 520. The refined fibrils of the cellulose suspension align in a nozzle. The fibrils of the cellulose suspension form an oriented fibril network in a nozzle 520.

The cellulose suspension 510 is directed onto a belt 500 via the nozzle(s) 520. The cellulose suspension exiting the nozzle 520 is shaped according to the nozzle outlet opening. The nozzle outlet opening may be shaped as a round or as elliptic, for example. The cellulose suspension exits the nozzle 520 in a form of a continuous strand having a cross-sectional shape corresponding to that of the nozzle outlet opening. The cellulose suspension exiting the nozzle 520 may have round or elliptic cross-sectional shape.

Two or more nozzles may be arranged adjacent, parallel along cross-sectional or transverse belt surface. Cross/transverse dimension refers to a width dimension of the belt; perpendicular to a longitudinal dimension of the belt, which corresponds to the moving direction of the belt. The two or more nozzles may be united, form an integrated unit. The distance between two adjacent nozzles may be in order of 0.5-50 mm, or 0.5-20 mm, for example 1 mm. The multiple nozzles may be placed next to each other along the whole cross dimension of the belt. In such case the whole cross dimension of the belt is covered with injected cellulose suspension at the same time via multiple nozzles.

During drying water is removed and fibrils star forming hydrogen bonds. Thereby fiber is formed. Hydrogen bonds are formed when dry content is from 70 wt-% to 100 wt-%. Dried cellulose suspension or fiber forming or fiber refer to dry content of at least 70 wt-%.

The cellulose suspension exit from a nozzle and/or injection onto a surface may be controlled hydraulically or pneumatically. Velocity of the cellulose suspension exiting the nozzle may be controlled by pressure applied on the cellulose suspension at the nozzle.

An oil supply 530 may be placed before the nozzle(s) 520 in relation to the moving direction of the belt 500. The oil supply 530 may be arranged to move, in an oscillating manner along cross dimension of the belt 500, perpendicular with direction of movement of the belt 500. The oil supply 530 is arranged after fiber extraction phase. Oil is supplied on the surface of the belt 500. The cellulose suspension is injected on an oily belt surface.

The cellulose suspension is dried on the surface of the belt 500. This may be effected internally and/or externally. Heating internally may be effected via the belt, e.g. by an electric heating resistor, heating steam or air. Heating externally may be effected via irradiation, heating and/or air blow. The dried cellulose suspension forms a fiber 550 onto surface of the belt 500. The fiber 550 is extracted from the surface of the belt 500. Extracting may be based on blowing, suction, vacumization, scraping or dropping fibers from the surface based on gravitation. The fiber 550 may be extracted mechanically or using vacuum or pressurized air. The extraction may be implemented manually or automatically. An extractor may be placed on any part of the belt 500, where the dryness of the fiber is at a desired level, for example over 70 wt-%. The extractor may be placed at end of the belt, or at either external side of the belt, wherein upper external side of the belt is arranged to move at opposite direction than the lower external side of the belt. It is possible to convey cellulose suspension or fiber on another belt for further drying.

Oil is supplied on a belt surface before the cellulose suspension is injected onto the surface. Oil may be replaced by a suitable substance.

The extracted fiber 560 is in form of unoriented and entangled fiber based raw wool, which may comprise uneven clumps among fluffy fiber based raw wool. When the fiber based raw wool comprises continuous fiber, the length of fiber is arranged to be cut, shortened or refined to form staple fibers. After shortening fiber based raw wool comprising staple fibers is formed.

The fiber comprises linear mass density of 1-20 dtex, which relates to an amount of mass per unit length (1 tex=1 g/1000 m; and 1 decitex=1 dtex=1 g/10000 m). Tenacity of the fiber comprises 10-30 cN/tex, preferably 15-25 cN/tex. Tenacity of the fiber comprises 15-25 cN/tex, preferably 15-20 cN/tex. Stretch to break or elongation break of the fiber comprises 5-15%, preferably 5-10%. Some of the oil from the drying surface is present in the fiber surface. The oil on the fiber surface has effect on further processing of the fiber based raw wool, for example to the friction and adhesion between fibers of the raw based wool.

Figure 6:
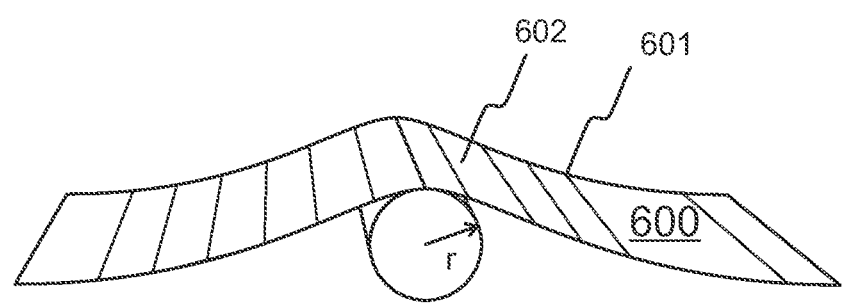
FIG. 6 illustrates a belt according to an embodiment.

FIG. 6 illustrates a belt according to an embodiment of the invention. FIG. 6 shows belt 600 comprising curved and grooved surface. FIG. 6 shows a belt for forming staple fibers, while in case of even, flat, non-curved belt a continuous fiber is formed on the belt. The curved surface of the belt comprises a radius of curvature of 0.25-4 m.

Grooves 601 are arranged onto external surface of the belt 600. The grooves 601 are arranged along a transverse direction of the belt 600, perpendicular to the longitudinal dimension or direction of movement of the belt 600. The injected cellulose suspension is in contact with ridges 602 between the grooves 601 of the belt surface. Grooves 601 form a weak point for the cellulose suspension and have effect of forming a discontinuity for the continuously injected cellulose suspension. The continuouosly injected cellulose suspension has a break at each groove. Thereby the cellulose suspension forms separate parts of length of ridges 602 between the grooves 601. After extensive water is dried, staple fibers are formed onto the belt, on the ridges 602 between the grooves 601. Length of formed staple fibers is determined by the length between grooves 601 on the belt surface.

In case of grooved belt, the fiber based raw wool extracted from the belt comprises staple fibers. No additional refining, shorting or cutting means or phases are needed. The staple fiber based raw wool is processable. The fiber based raw wool comprises staple fibers, which have been shortened to a predefined length with the aid of grooves. The spacing between the grooves on the belt surface determine length of the staple fibers.

The grooves 601 on the surface may be replaced by other kind of discontinuation places. Discontinuation places may comprise grooves or ridges. Discontinuation places may comprise cut-outs, inlays, slots, channels, crests, indentations, ridges, protrusions, projections or other kind of discontinuation places. The discontinuation places comprise irregular surface shape. The regular, even or steady surface comprises irregularities at certain intervals. The discontinuation places or irregularities of the surface are aligned on the surface perpendicular to the direction of movement of the surface.

Alternatively or in addition, the continuously injected cellulose suspension may be cut into staple fibers by exposing the dried/drying fiber to an external matter or means for cutting. The external matter or means for cutting may relate to radiation, substance or other matter capable of cutting the fiber on the surface to staple fibers. The external matter or cutting means may comprise laser, infrared, heat, ultrasound, electron beam, water or chemicals, for example. The fiber may be cut after or while dried on the surface.

Figure 7:
FIG. 7 illustrates a staple fiber according to an embodiment.
Figure 8:
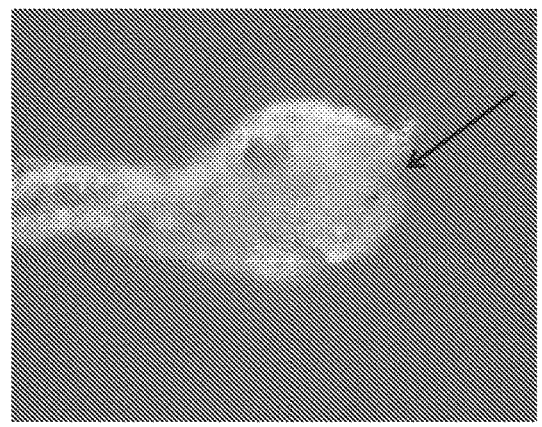
FIG. 8 illustrates a staple fiber according to an embodiment.

When the continuous fiber is shortened as staple fibers, cut end of a staple fiber is sharp, or at least substantially sharp. Sharp cut end is illustrated in a FIG. 7. When staple fiber is formed on a curved, grooved surface by the grooves, the end of the staple fiber is uneven or irregular in comparison to the sharp cut end of a staple fiber. FIG. 8 shows end of a staple fiber, which has been formed by a curved, grooved surface. Groove causes interruption to the applied continuous cellulose suspension, thereby forming separated portions of certain length, which, after dried, form staple fibers.

Such interrupted surface of a staple fiber may show fibrils or smaller portions. In an extended view, uneven end surface of interruption shows irregular shape.

The grooves on the surface may be replaced by cut-outs, inlays, slots, channels, crests, indentations, ridges, protrusions, projections or other kind of discontinuation places of the surface. Alternatively or in addition, the continuously injected cellulose suspension may be cut into staple fibers by exposing the cellulose (suspension)/fiber on the surface to an external matter. The external matter may relate to radiation, substance or other matter capable of cutting the fiber on the surface to staple fibers. The external matter may comprise laser, infrared, heat, ultrasound, electron beam, water or chemicals, for example. The cellulose suspension may be cut after or while dried on the surface.

Figure 9:
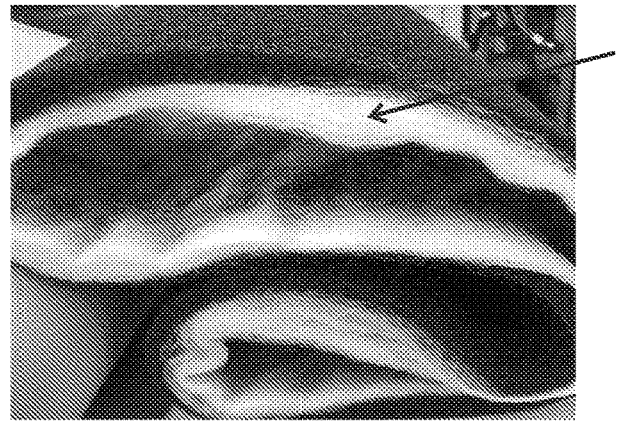
FIG. 9 illustrates a fiber based raw wool according to an embodiment.

FIG. 9 shows a fiber based raw wool arranged on a conveyor belt. Staple fibers are extracted from cylinder to a moving conveyor belt where they are arranged in a random, bulky network.

The surface, of e.g. a belt or a cylinder, may comprise hydrophobic surface material. External surface of a cylinder or a belt may be covered with a nonporous hydrophobic polymer coating. The polymer coating has effect of forming a hydrophobic surface. The hydrophobic polymer coating may be covered with oil. The coating and oil coverage of the surface enable to achieve a hydrophobic, low friction and low contact angle hysteresis external surface. The oil effects on cellulose suspension remaining in contact with the external surface via the oil. The polymer coating and oil on the surface and/or centripetal force of a rotating cylinder enable controlling and maintaining round cross-sectional shape of the cellulose suspension injected on the surface. Oil and low contact angle hysteresis on the outer surface of the cylinder or the belt have effect on maintaining the round cross-sectional shape of the cellulose suspension during drying. Oil has effect of reducing risk of the cellulose solution adhering to the surface. Oil has effect of providing stable cross-sectional shape fiber and/or avoid formation of unwanted wide, thin and/or weak ribbons on the surface. Part of the oil remains with the fiber and acts as finishing agent. Oil may be used for example to control friction between fibers and/or between fibers and metal during processing. These are desired parameters for processing the fiber based raw wool during further processing and formation of products, like yarn, non-woven or other. Oil coverage of the surface may be replaced by other suitable substance, which may have at least some/all similar properties with oil. For example, oil may be replaced with wax.

The cellulose suspension directed through a nozzle onto a surface is dried on the surface. Drying is accomplished via heat and, in case of a cylinder, a rotating motion of a cylinder. Rotation of the cylinder and/or heating enable drying of provided cellulose suspension on the surface. A continuous fiber may be formed on the surface. Alternatively, stable fibers may be formed on the surface. The cellulose suspension may be dried externally and/or internally via the surface of a cylinder or of a belt. The cylinder or the belt may comprise a heating element. The cylinder or the belt may comprise an internal heater. The internal heater may implement heating electronically, via a resistor, or via hot steam. The cylinder or the belt may comprise an external heater. The external heater may provide irradiation or air blow or steam blow towards the surface in order to dry the cellulose suspension on the surface. The heater(s) enable drying cellulose suspension applied on the surface. Heater or heating elements are arranged to dry the cellulose suspension by removing water.

Oil is applied on the surface. Oil on the surface has effect of reducing surface tension, friction and/or surface contact angle hysteresis. Oil may comprise, but is not limited to, fiber finishing oils to reduce fiber-fiber friction or fiber-metal friction, or a vegetable oil or a non-immiscible fluid. Oil may be replaced by other suitable substance that has effect of reducing surface tension, friction and/or surface contact angle hysteresis.

The surface is arranged to move and convey the injected cellulose suspension. The surface may comprise grooves. Staple fibers may be formed on a curved and grooved surface. The surface may comprise a curver or round cylinder surface, or a curved belt surface. The grooves are aligned transverse to the direction of movement of a surface. Grooves are arranged transverse to the direction of movement of a belt. The grooves extend along transverse direction of the belt, which is perpendicular to the longitudinal dimension, or direction of movement of the belt. Grooves are arranged transverse to the direction of rotation of a cylinder. The grooves extend along length direction of the cylinder, being in parallel with the axis of rotation of the cylinder. The surface comprises thin grooves, in comparison to wide ridges between the grooves. The ridges of the surface form support surface for injected cellulose suspension, while grooves form a discontinuation places. Grooves and the ridges between them enable forming staple fibers on the surface. Injected cellulose suspension is arranged to break at a groove. Spacing between the grooves is configured to define length of formed staple fibers.

Width of the grooves may be 0.5-5 mm, preferably 2-3 mm. Depth of the grooves may be 0.5-10 mm, preferably 2-3 mm.

The grooves on the surface may be replaced by other kind of discontinuation places of the surface. A discontinuation place may comprise grooves or ridges. Ridges may comprise sharp external edges. Ridge height from the surface may be of 0.5-3 mm, or preferably 1-2 mm. A discontinuation place may comprise grooves, ridges, cut-outs, inlays, slots, channels, crests, indentations, protrusions, projections or other kind of discontinuation places of the surface. The discontinuation places are arranged transverse to the direction of movement of the surface. The discontinuation places extend along width direction the surface, being in parallel with the axis of rotation of a cylinder or perpendicular with a direction of movement of a belt or a wire. The surface comprises thin discontinuation places, in comparison to wide regular surfaces between the discontinuation places. The regular surfaces support the injected cellulose suspension, which is arranged to break at discontinuation places. The surface comprising discontinuation places enable forming staple fibers on the surface. Spacing between the discontinuation places is configured to define length of formed staple fibers.

Alternatively or in addition, the continuously injected cellulose suspension may be cut into staple fibers by exposing the fiber to an external matter or cutting means. The external matter may relate to radiation, substance or other matter capable of cutting the fiber on the surface to staple fibers. The external matter or cutting means may comprise laser, infrared, heat, ultrasound, electron beam, water or chemicals, for example. The cellulose suspension may be cut after or while dried on the surface.

Centripetal force of a moving surface, hydrophobic properties of a surface and oil properties have effect on preserving round cross section of the the injected cellulose suspension and fiber, as its dried form, on the surface.

As free water is removed from the cellulose suspension during drying, hydrogen bonds start to appear. This occurs on/after solid content of the cellulose suspension exceeds fiber content of 70 wt-%.

The dried cellulose solution forms a continuous fiber (strand) onto a continuous surface. Grooved and curved surface enable forming of stable fibers without additional refining or shortening after drying. The staple fibers comprise length of 6-80 mm, preferably 30-70 mm. The grooves on the surface may be replaced by other kind of discontinuation places of the surface. Alternatively or in addition, the continuously injected cellulose suspension may be cut into staple fibers by exposing the cellulose (suspension) to an external matter or to means for cutting. The external matter or the means for cutting may relate to radiation, substance or other matter capable of cutting the cellulose (suspension) on the surface to staple fibers. The external matter or cutting means may comprise laser, infrared, heat, ultrasound, electron beam, water or chemicals, for example. The cellulose suspension may be cut before, after or while dried on the surface. Long fibers or staple fibers may be interlocked together in order to form a permanent network of fibers. Disintegration of the hydrogen bonds, may be done by exposing the staple fibers to water or aqueous solution. A minor mechanical or hydrodynamical force, like a pull or a twist or a hydrodynamic shear, disintegrates a wetted staple fiber composition or product. When exposed to water, the staple fibers will return into separate primary cellulosic fibrils. This enables forming water disposable products.

The natural fiber based raw wool comprises large specific surface area and low density. It provides good filtering properties and a good insulator, while it's thermal conductivity is low. Due to uneven fiber surface, the natural fiber based raw wool comprises high friction, which is desired property for further processing, for example manufacturing non-woven material.

The natural fiber based raw wool comprises good water absorption and water retention properties. Water retention of the natural fiber based raw wool may be 10-100 times it's own weight.

The fiber based raw wool may be processed as a raw wool sheared from a sheep. The fiber based raw wool comprises staple fibers. The fiber based raw wool comprises staple fibers in fluffy arrangement, in unorganized, unoriented order and forming clumps or conglomerates of different densities.

The fiber based raw wool may be carded. Generally carding orients, detangles and cleans raw wool towards oriented strands. Carding may be performed by a card, by a carding machine, by heckling machine. Carding machine may have surface covered with carding clothing or soft-bristled brush attachment. During carding the staple fibers orientate towards common fiber orientation and the staple fiber density becomes more even, while reducing clumps. Due to carding fibers tend to orient similarly, thereby having substantially similar orientation among longitudinal dimension of fibers. The carded fiber based raw wool comprises at least mainly oriented staple fibers and density variations or clumps are reduced. The structure tends to become more homogenous during carding.

Natural fiber based raw wool has properties desired during carding, like low friction between fibers and/or between fibers and metal (of cards).

The carded fiber based raw wool may be processed as a yarn or as a non-woven material. Yarn may be made from carded fiber based raw wool by forming a continuous pre-yarn and spinning several pre-yarns as a yarn. The yarn may be used for manufacturing textiles of different kind. A textile may be made of yarn using known textile manufacturing processes and equipments. Many kind of end products including yarn, rope, textile, fabric and products including such, may be made of yarn produced of natural fiber based raw wool.

The non-woven material may be produced from the carded fiber based raw wool by a non-woven process, or felting, for example needle punch, hydro-entanglement or other suitable method. The non-woven process binds the staple fibers mechanically in order to produce continuous non-woven material or fabric. Adhesive may be added in order to enhance bonding.

Non-woven material may be used to manufacture hygiene products. The hygiene products may be disposed with water, whereby the product breaks down to cellulose fibrils. The hygiene products may comprise flushable products, which disintegrate into water. Hygiene products may comprise wipes or diapers. The products made of the staple fiber based raw wool have firm fabric and feel, when those are dry. However, underlying fibrils are small and locked together via hydrogen bonds, which become very weak at aqueous environment. Once in water, even a low shear will cause staple fibers to disintegrate back to sorter cellulose fibrils. In addition to disposability, the non-woven material made of staple fiber based raw wool has ability to absorb and retain water. This ability is desired for products like diapers and alike.

Yarn made of natural fiber based raw wool may have yarn count of 5-200 tex. The yarn comprises tenacity of 5-15 cN/tex; and elongation at break of 3-10%. Non-woven material made of natural fiber based raw wool comprises density of 10-100 kg/m$^3$.

The manufacturing process enables providing yarn and/or non-woven material economically and environmentally friendly way. The provided fiber based raw wool is provided by compact manufacturing phase, even as a single process. The fiber based raw wool is processable with process and equipment known from raw wool processing and handling. The fiber based raw wool may be processed as yarn using yarn spinning equipment or as non-woven material using non-woven process and method.

The staple fiber based raw wool or products have effect on biodegradability. Discarding is ecological and use of natural based cellulosic fibers enables recycling and reuse.

A natural fiber based raw wool may be used as an insulator. It forms a usable insulator before or after carding.

Figure 10:
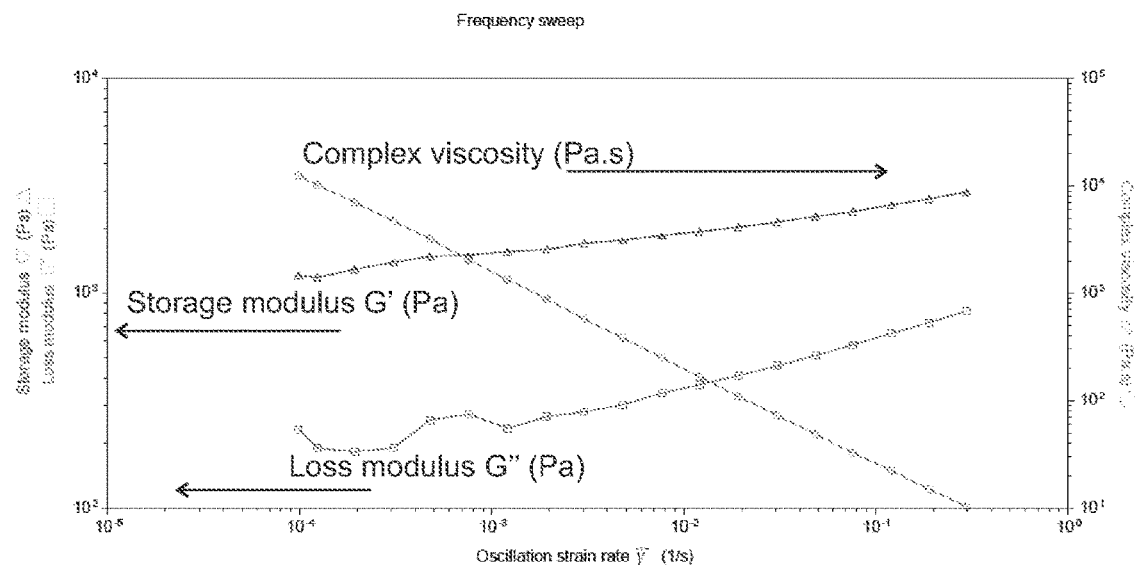
FIG. 10 illustrates gel properties of MFC suspension according to an embodiment.

FIG. 10 illustrates gel properties of the MFC suspension. In this suspension the gel strength, being a storage modulus, is adjusted to a desired level, being above 1000 Pa, using rheology modifier.

Figure 11:
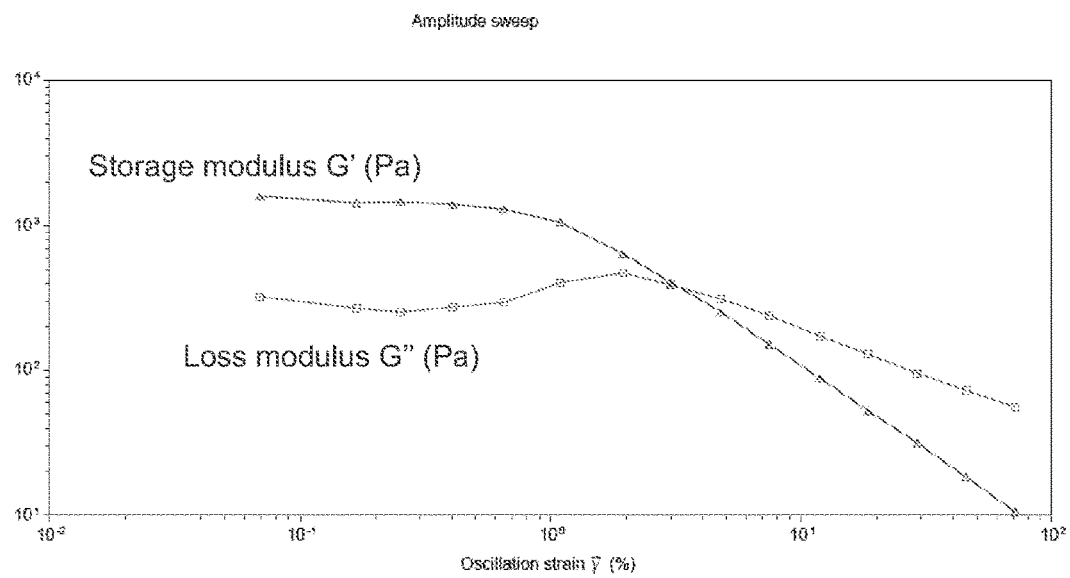
FIG. 11 illustrates gel properties according to an embodiment.

FIG. 11 illustrates gel properties where yield point, being a storage and loss modulus intersection, is adjusted to 2% using rheology modifier.

Figure 12:
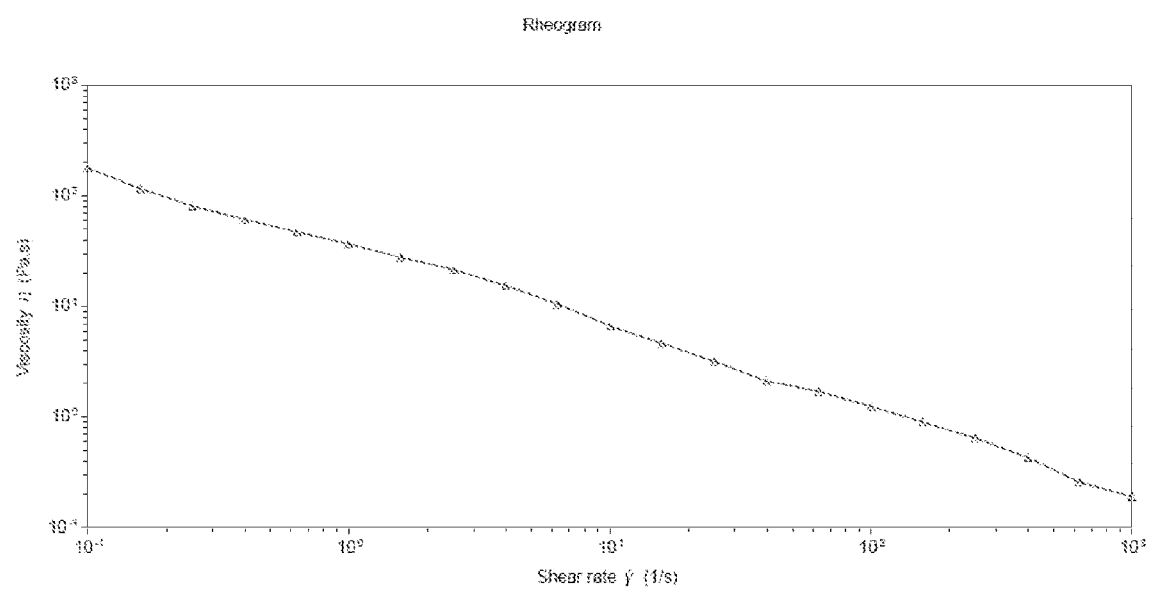
FIG. 12 illustrates an example rheogram according to an embodiment.

FIG. 12 illustrates an example rheogram showing high shear thinning behavior. Shear viscosity is adjusted to 0.2 Pa at 1000 1/s shear rate using rheology modifier.

The previously presented description is presented as illustrative of aspects of the invention. Parts or details may be replaced, changed, combined or omitted without departing from the scope of the invention as defined in the claims.

The invention claimed is:

1. A method for manufacturing natural fiber based staple fibers comprising:
   providing a cellulose suspension including refined cellulose fibrils,
   directing the cellulose suspension through a nozzle onto a surface,
   drying the cellulose suspension onto the surface, and
   cutting the cellulose suspension on the surface for forming staple fibers.

2. The method according to claim 1, wherein the refined cellulose fibrils comprise refined plant based cellulose fibrils.

3. The method according to claim 1, wherein the cellulose suspension exiting the nozzle comprises a shape of the nozzle outlet opening, optionally a round or an elliptic cross-sectional shape.

4. The method according to claim 1, wherein the drying comprises drying the cellulose suspension on the surface via radiation, blow or conduction.

5. The method according to claim 1, further comprising applying oil or wax to the surface.

6. The method according to claim 1, further comprising drying the cellulose suspension onto the surface to a dry concentration of at least 70 wt % and/or wherein drying comprises forming chemical bonds between the refined cellulose fibrils.

7. The method according to claim 1, wherein the staple fibers have a length of 6-80 mm.

8. The method according to claim 1, wherein cutting the cellulose suspension on the surface for forming staple fibers comprises exposing the cellulose suspension to cutting means before, after or while drying the cellulose suspension onto the surface.

9. The method according to claim 1, further comprising extracting the staple fibers from the surface for forming natural fiber based raw wool comprising staple fibers.

10. The method according to claim 9, further comprising carding the natural fiber based raw wool in order to orient and entangle the fibers, optionally further comprising processing the fiber based raw wool to a pre-yarn and spinning the pre-yarn into a yarn; or processing the natural fiber based raw wool to the form of non-woven material.

11. An apparatus for manufacturing natural fiber based staple fibers comprising:
   a nozzle arranged to direct a cellulose suspension including refined cellulose fibrils onto a surface, and
   a dryer arranged to dry the cellulose suspension on the surface for forming a fiber, wherein the cellulose suspension or the fiber is arranged to be cut on the surface for forming staple fibers.

12. The apparatus according to claim 11, wherein the dryer comprises at least one of a heating resistor, a radiator, a vaporizer or a blower, and wherein the dryer is arranged to dry the cellulose suspension.

13. The apparatus according to claim 11, wherein the surface comprises a hydrophobic external surface.

14. The apparatus according to claim 11, wherein the apparatus comprises means for cutting, and wherein the cellulose suspension is exposed to the means for cutting on the surface, wherein the means for cutting optionally comprises at least one of the following: a discontinuation place(s) on the surface, radiation, laser, infrared, heat. ultrasound, electron beam, water or chemical.

15. The apparatus according to claim 14, wherein the means for cutting comprises discontinuation places on the surface, and wherein the discontinuation places are aligned on the surface perpendicular to the direction of movement of the surface, at certain predetermined intervals, further wherein the predetermined intervals between the discontinuation places on the surface optionally have a length of 6-80 mm, and wherein the discontinuation places optionally have an irregular surface shape.

16. The apparatus according to claim 11, wherein the surface comprises a curved surface.

* * * * *